United States Patent
Kuzelka

(10) Patent No.: US 11,679,215 B2
(45) Date of Patent: Jun. 20, 2023

(54) METHODS AND SYSTEMS FOR WASTE GAS DETECTION IN AN ANESTHETIC VAPORIZER

(71) Applicant: GE Precision Healthcare LLC, Milwaukee, WI (US)

(72) Inventor: Russell James Kuzelka, McFarland, WI (US)

(73) Assignee: GE Precision Healthcare LLC, Milwaukee, WI (US)

(*) Notice: Subject to any disclaimer, the term of this patent is extended or adjusted under 35 U.S.C. 154(b) by 818 days.

(21) Appl. No.: 16/686,049

(22) Filed: Nov. 15, 2019

(65) Prior Publication Data
US 2021/0146076 A1    May 20, 2021

(51) Int. Cl.
*A61M 16/00* (2006.01)
*A62B 19/00* (2006.01)

(52) U.S. Cl.
CPC .... *A61M 16/0093* (2014.02); *A61M 16/0003* (2014.02); *A62B 19/00* (2013.01); *A61M 2202/0241* (2013.01); *A61M 2202/049* (2013.01)

(58) Field of Classification Search
CPC ...... A61M 16/0093; A61M 2202/0241; A61M 16/104; A61M 16/183; A61M 16/18; A61M 16/10; A62B 19/00
See application file for complete search history.

(56) References Cited

U.S. PATENT DOCUMENTS

| | | | |
|---|---|---|---|
| 3,592,191 A | 7/1971 | Jackson | |
| 6,536,430 B1 | 3/2003 | Smith | |
| 2001/0025640 A1* | 10/2001 | Pessala | A61M 16/0093 128/205.27 |
| 2006/0254586 A1* | 11/2006 | Berry | A61M 16/0093 128/203.14 |
| 2009/0078254 A1 | 3/2009 | Rock | |
| 2010/0078018 A1* | 4/2010 | Heinonen | A61M 16/01 128/202.22 |
| 2010/0269820 A1* | 10/2010 | Danielsen | A61M 16/0051 128/203.14 |
| 2013/0126464 A1* | 5/2013 | Manzke | B65B 3/04 141/2 |
| 2015/0273172 A1* | 10/2015 | Pessala | A61M 16/0069 128/203.12 |

* cited by examiner

*Primary Examiner* — Margaret M Luarca

(57) ABSTRACT

Systems and methods are provided for detecting and sequestering waste anesthetic gases released by an anesthetic vaporizer. In one embodiment, a method for an anesthetic vaporizer installed in an anesthesia machine includes detecting an emission of waste anesthetic gases (WAGs) from the anesthetic vaporizer, and responsive to detecting the emission of WAGs, performing at least one of scavenging the WAGs and outputting an alert.

16 Claims, 7 Drawing Sheets

METHODS AND SYSTEMS FOR WASTE GAS DETECTION IN AN ANESTHETIC VAPORIZER

FIELD

Embodiments of the subject matter disclosed herein relate to anesthesia systems, and more particularly, to systems and methods for monitoring an air quality surrounding an anesthetic vaporizer.

BACKGROUND

During some medical procedures, such as surgical procedures, a patient may be placed under general anesthesia by administrating an anesthetic agent. In some examples, the anesthetic agent may be a volatile anesthetic agent that is administered to the patient via an anesthetic vaporizer. For example, the anesthetic vaporizer may induce and control vaporization of the volatile anesthetic agent from a liquid form. A carrier gas (e.g., a mixture of oxygen and fresh air) may flow into the vaporizer and blend (e.g., mix and converge) with the anesthetic agent vapors before flowing to the patient, where they may be introduced via inhalation, for example, via a mask or breathing tube.

Anesthetic vaporizers may emit waste anesthetic gases (WAGs) during operation, resulting in a portion of the anesthetic agent vapors diffusing throughout the surrounding area. For example, WAGs may escape from around the mask or breathing tube. In another example, WAGs may escape from various coupling locations within the anesthetic vaporizer. In still another example, refilling the anesthetic vaporizer outside of a fume hood may result in the release of WAGs.

BRIEF DESCRIPTION

In one embodiment, a method for an anesthetic vaporizer installed in an anesthesia machine includes detecting an emission of waste anesthetic gases (WAGs) from the anesthetic vaporizer, and responsive to detecting the emission of WAGs, performing at least one of scavenging the WAGs and outputting an alert. In this way, the emission of WAGs may be detected and mitigated.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
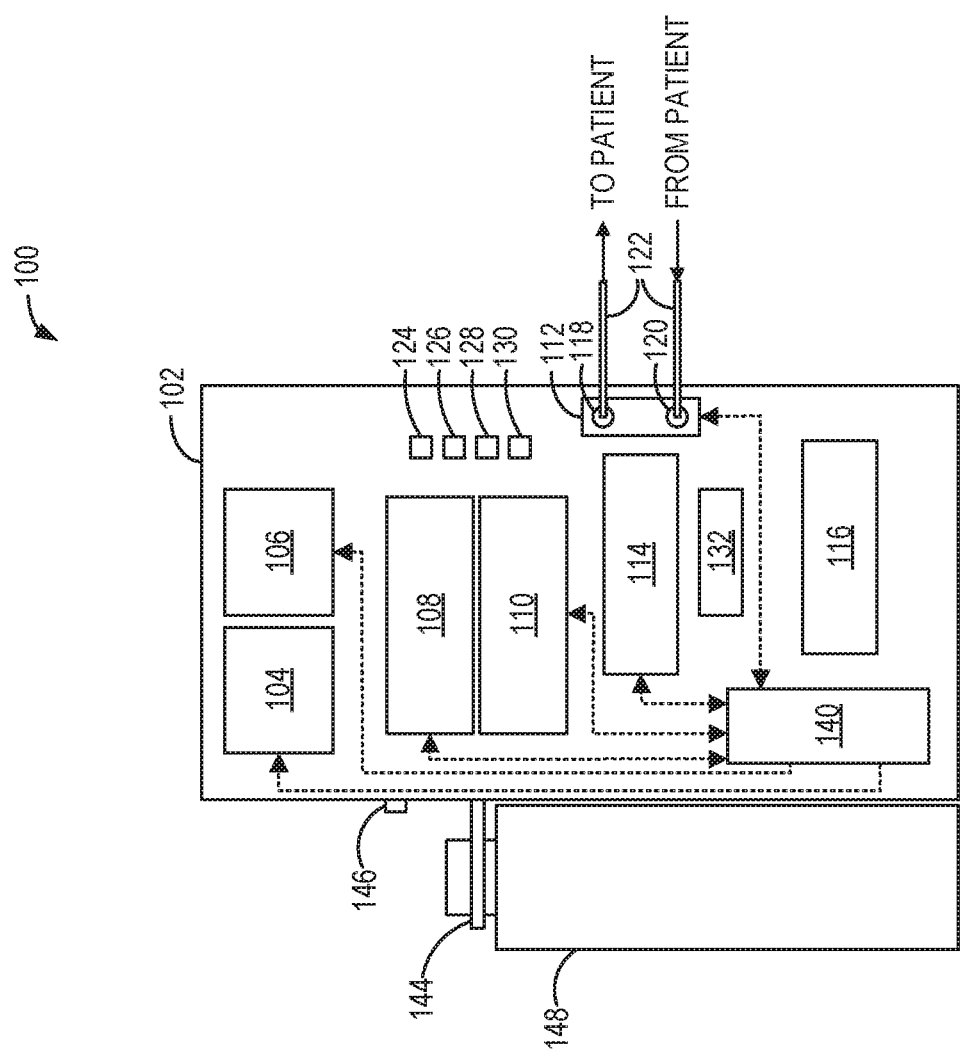
FIG. 1 schematically shows an exemplary embodiment of an anesthesia machine.

The following description relates to various embodiments for actively monitoring the emission of waste anesthetic gases (WAGs) during medical procedures. Anesthetic gases may be intentionally generated for delivery to a patient using an anesthetic vaporizer included in an anesthesia machine, but in some examples, small amounts of anesthetic gases, known as WAGs, may be released to the surrounding environment (e.g., an exam room or surgical suite). The emission of WAGs may occur during both anesthetic vaporizer refilling and anesthetic agent administration. As one example, WAGs may be generated during refilling, particularly if the anesthetic vaporizer includes a "fill during use" capability that enables the anesthetic vaporizer to be refilled with liquid anesthetic agent without being dismounted from the anesthesia machine. As such, the refilling may not occur within a fume hood, which may otherwise prevent WAG release. As another example, leaks at coupling sites within the anesthetic vaporizer, such as due to seal degradation, may allow WAGs to diffuse into the surrounding environment. As yet another example, WAGs may escape from around the patient's anesthesia mask or tube, especially if an incorrect size is used and/or the mask or tube is poorly fit to the patient. Currently available anesthetic vaporizers do not have the capability to actively monitor for the presence of WAGs. As a result, healthcare professionals using the anesthesia machine may not be alerted to leaks or other WAG emissions. Because the WAGs may diffuse into the environment surrounding the anesthesia machine, healthcare professionals may be unintentionally exposed to the anesthetic agent. Overall, WAGs may decrease air quality in the environment surrounding the anesthesia machine.

Thus, embodiments described herein include systems for scavenging and sequestering the WAGs by suctioning WAGs in the vicinity of the anesthetic vaporizer through an adsorbent filter. In some embodiments, one or more sensors, including one or more volatile organic compound (VOC) sensors configured to detect WAGs, are provided that may be coupled to and/or within the anesthetic vaporizer. Output from the one or more sensors may be used by an electronic controller to determine when WAGs are being emitted by the anesthetic vaporizer. In one embodiment, the anesthetic vaporizer is connected to an active scavenging system of the anesthesia machine, which may be used to suction and filter the WAGs. In another embodiment, a fan or blower internal to the anesthetic vaporizer may draw ambient air and WAGs through a filter included in the anesthetic vaporizer. In some embodiments, the controller may output an alert responsive to a detected level of WAGs increasing above a threshold. Further, in some embodiments, the controller may output an alert to replace the filter included in the anesthetic vaporizer.

The embodiments disclosed herein may provide several advantages. For example, the VOC sensor(s) may detect real-time WAG emissions during use, allowing medical personal to proactively manage air quality in the clinical environment. Further, by actively monitoring for even small leaks within the vaporizer while in use, the WAG detection system may alert users to anesthetic vaporizer degradation, expediting anesthetic vaporizer repair. Further, by actively scavenging and/or sequestering WAGs around the anesthetic vaporizer, unwanted vapors may be removed from the clinical environment, increasing air quality. Further still, by monitoring filter usage, saturated adsorbent filters may be detected and replaced to ensure continued WAG scavenging functionality. Overall, by providing an active alerting system and an active scavenging system, WAG levels may be reduced in the clinical environment without the users of the anesthetic vaporizer having to closely monitor for leaks or other WAG emissions, freeing the operator to focus on patient monitoring or refilling, for example.

Figure 2:
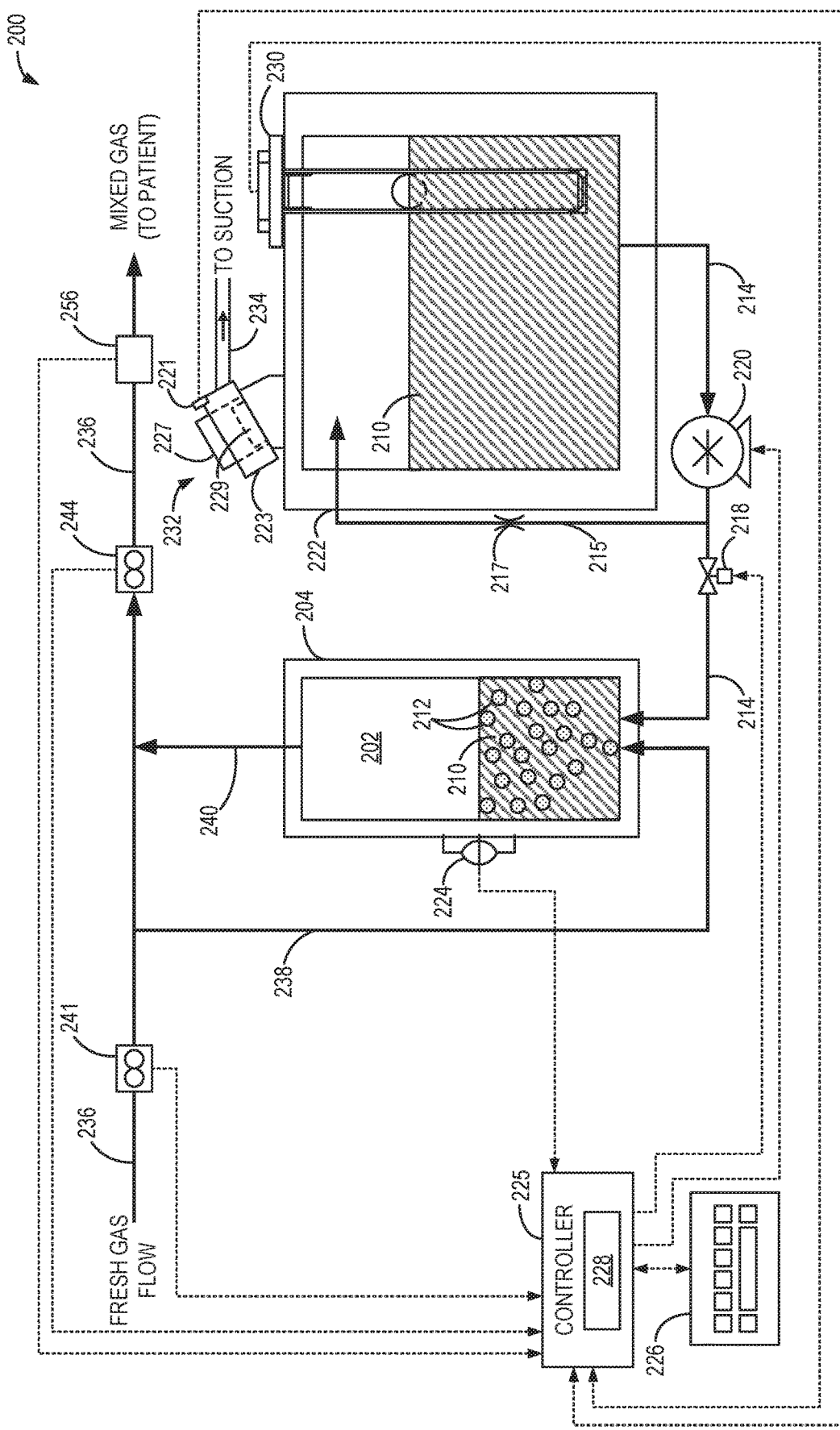
FIG. 2 schematically shows an exemplary embodiment of an anesthetic vaporizer that may be included in an anesthesia machine.
Figure 3:
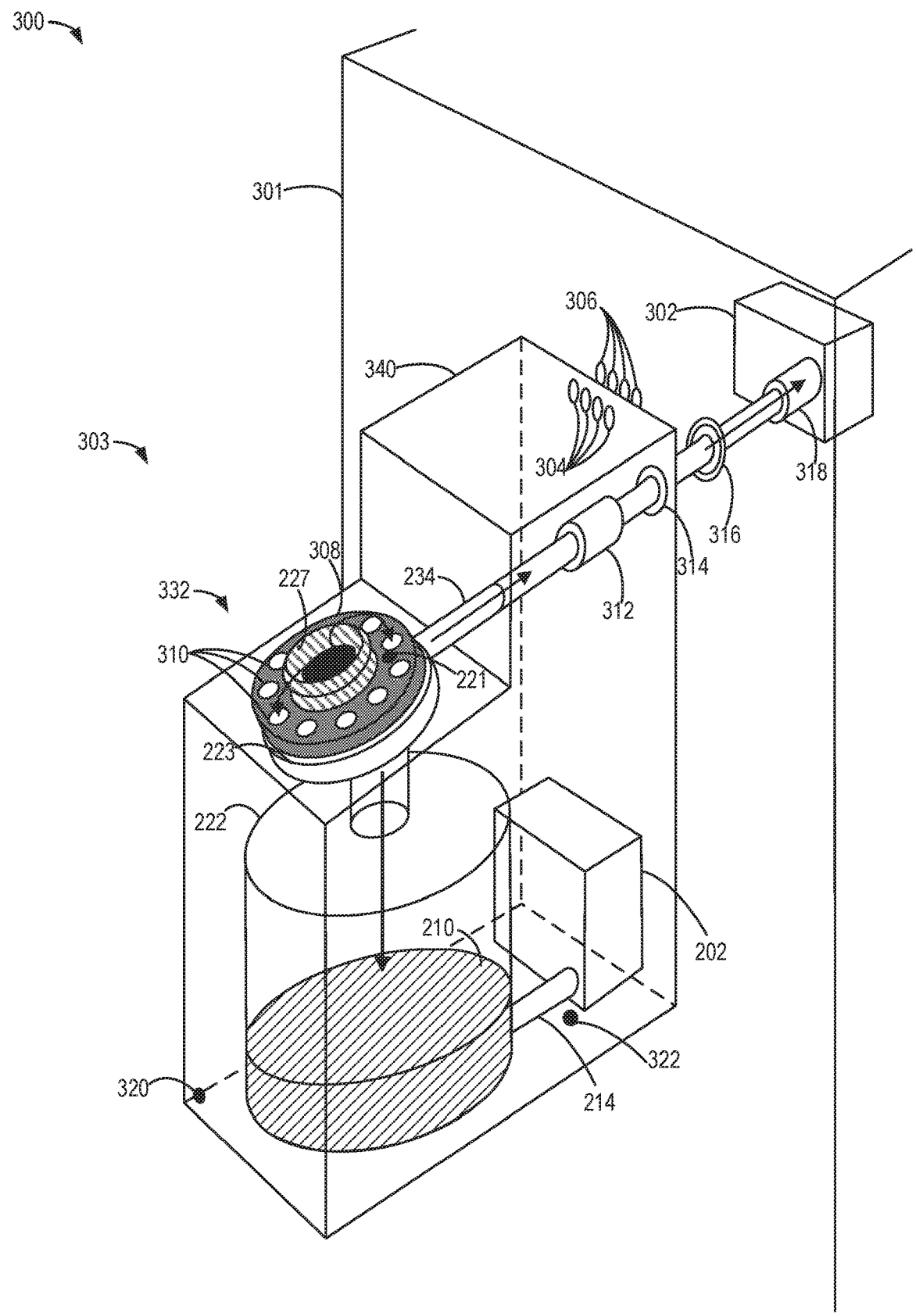
FIG. 3 schematically shows a first exemplary embodiment of a waste anesthetic gas (WAG) scavenging system that may be included in an anesthetic vaporizer, the first exemplary embodiment including an active scavenging connection to an anesthesia machine.
Figure 4:
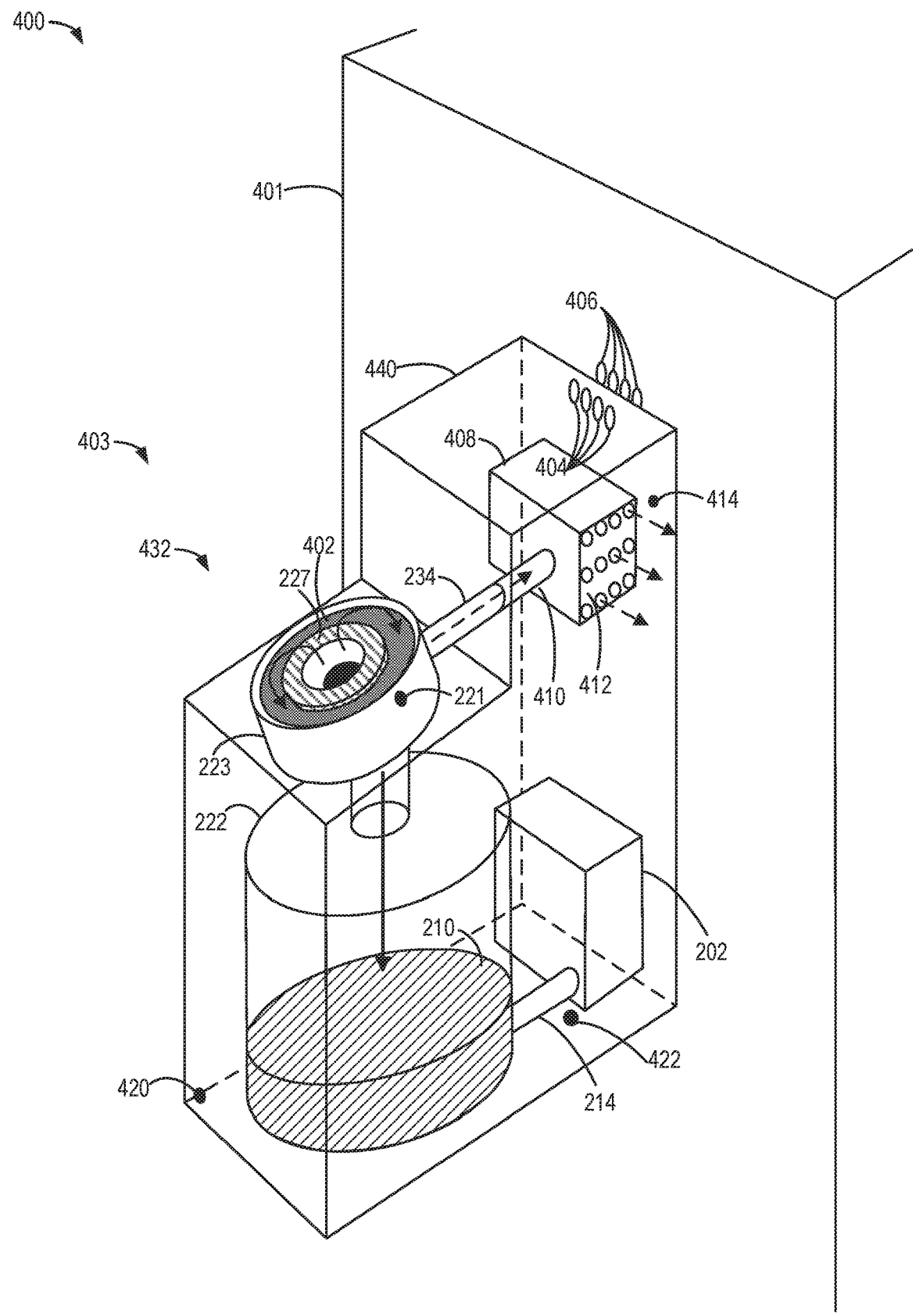
FIG. 4 schematically shows a second exemplary embodiment of a WAG scavenging system that may be included in an anesthetic vaporizer, the second exemplary embodiment including a sequestration filter cartridge.
Figure 6:
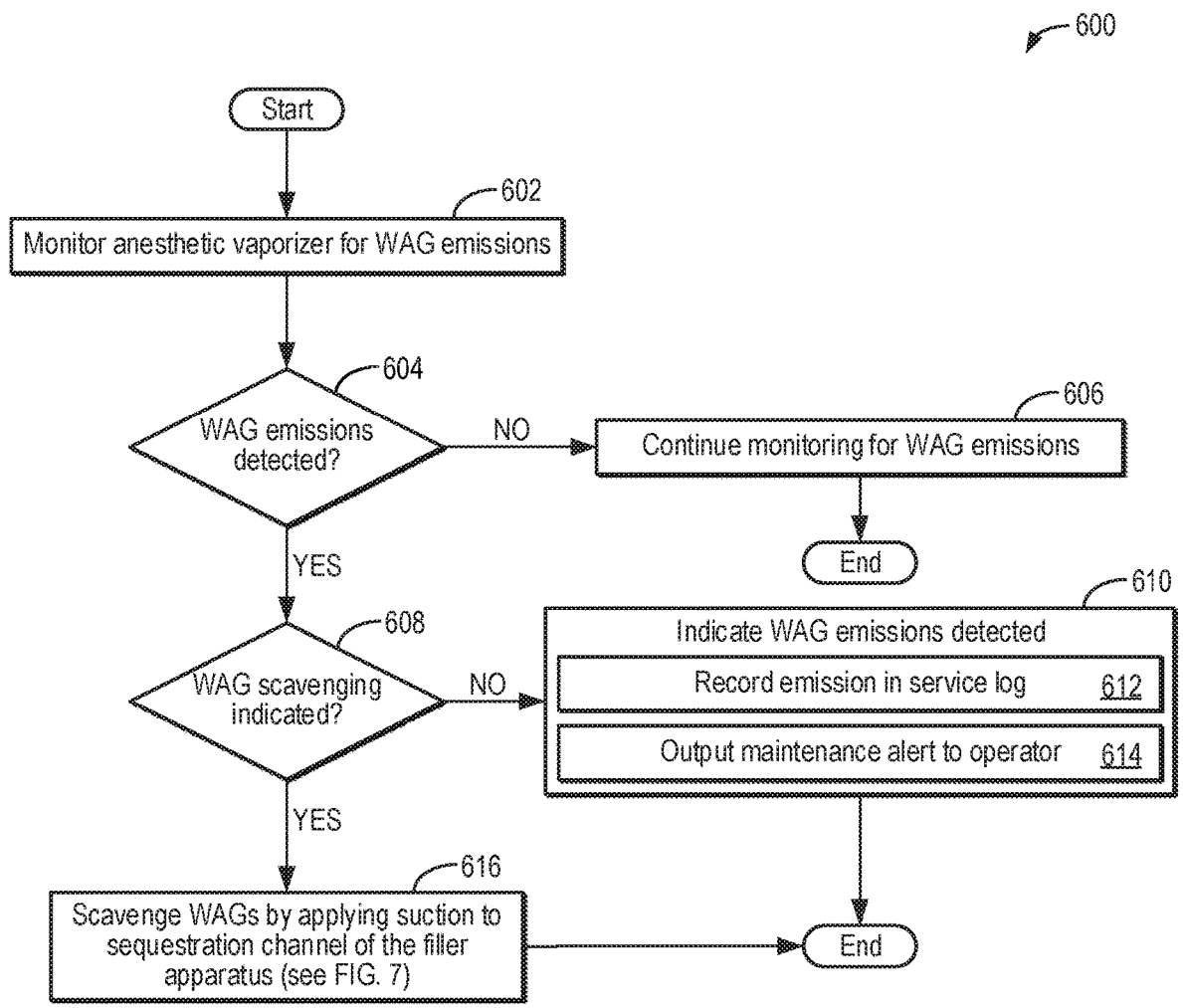
FIG. 6 is a high-level flow chart illustrating an exemplary embodiment of a method for identifying a release of WAGs by an anesthetic vaporizer.
Figure 7:
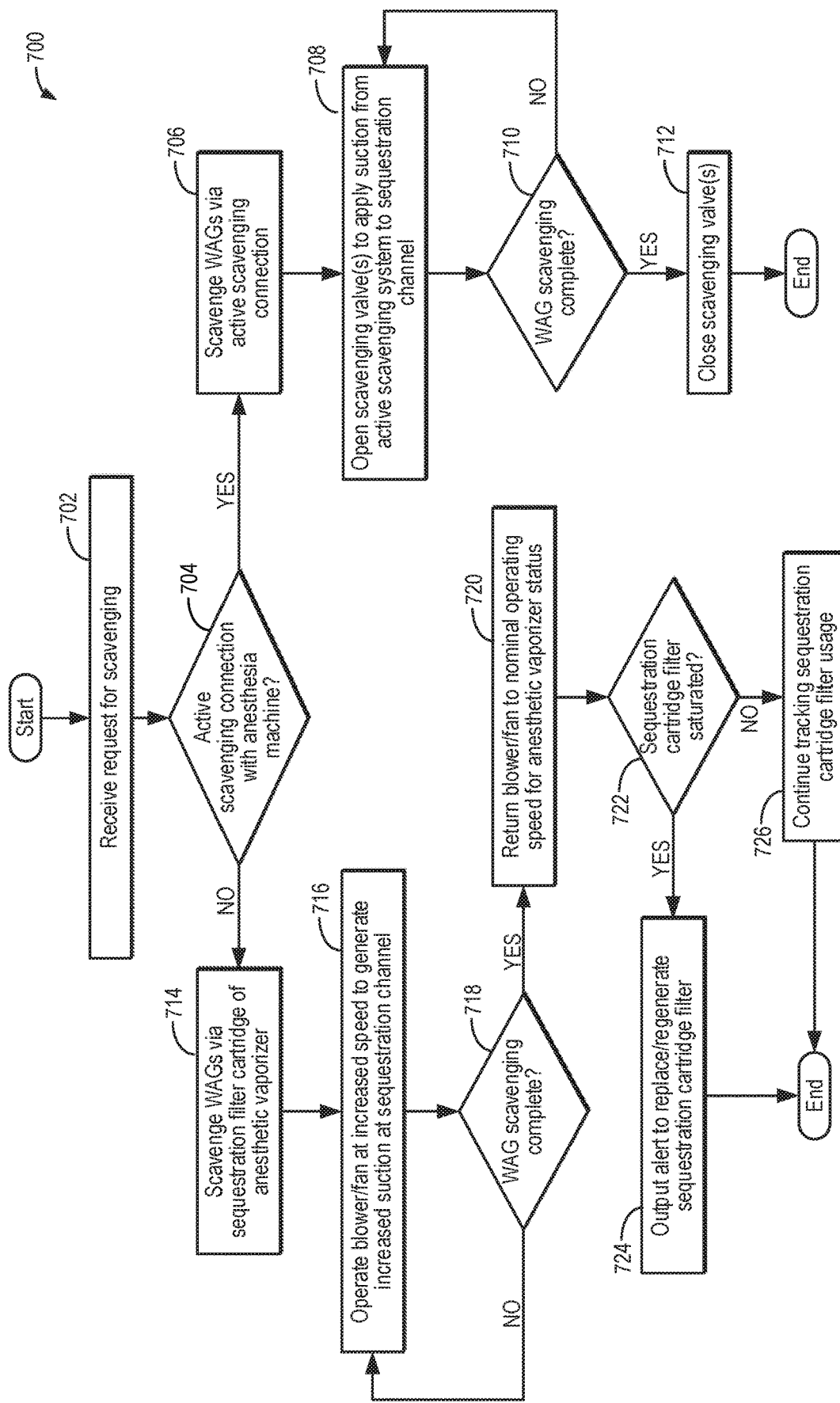
FIG. 7 is a flow chart illustrating an exemplary embodiment of a method for scavenging WAGs released by an anesthetic vaporizer.

FIG. 1 schematically shows an exemplary embodiment of an anesthesia machine. FIG. 2 shows an exemplary embodiment of an anesthetic vaporizer that may be included in the anesthesia machine of FIG. 1. FIG. 3 shows a first exemplary embodiment of a WAG scavenging system that may be included in the anesthetic vaporizer of FIG. 2, the first exemplary embodiment including a connection an active scavenging system that may be included in the anesthesia machine of FIG. 1. FIG. 4 shows a second exemplary embodiment of a WAG scavenging system that may be included in the anesthetic vaporizer of FIG. 2, the second exemplary embodiment including a sequestration filter cartridge. The sequestration filter cartridge is shown in more detail in FIGS. 5A-5B. Further, VOC sensors may be positioned at various locations on and/or near the anesthetic vaporizer, as shown in FIGS. 2-4. FIG. 6 depicts an example method for detecting the presence of WAGs due to leaks and anesthetic vaporizer refilling, and FIG. 7 shows an example method for sequestering the WAGs via the active scavenging system of the anesthesia machine (e.g., the first exemplary embodiment of the WAG scavenging system) or via the sequestration filter cartridge (e.g., the second exemplary embodiment of the WAG scavenging system). Thus, methods and systems are provided for reducing an amount of WAGs in a clinical and/or surgical environment, thereby increasing air quality and reducing inadvertent healthcare professional exposure to anesthetic gases.

Turning now to the figures, FIG. 1 schematically shows an example anesthesia machine 100. Anesthesia machine 100 includes a frame (or housing) 102. In some embodiments, frame 102 may be supported by casters, where the movement of the casters may be controlled (e.g., stopped) by one or more locks. In some examples, the frame 102 may be formed of a plastic material (e.g., polypropylene). In other examples, the frame 102 may be formed of a different type of material (e.g., metal, such as steel).

Anesthesia machine 100 also includes an anesthesia display device 104, a patient monitoring display device 106, a respiratory gas module 108, one or more patient monitoring modules, such as a patient monitoring module 110, a ventilator 112 (explained in more detail below), an anesthetic vaporizer 114, and an anesthetic agent storage bay 116. Anesthesia machine 100 may further include a main power indicator 124, a system activation switch 126 (which, in one example, permits gas flow when activated), an oxygen flush button 128, and an oxygen control 130. An example embodiment of anesthetic vaporizer 114 will be described below with respect to FIG. 2. Anesthetic vaporizer 114 may vaporize the anesthetic agent and combine the vaporized anesthetic agent with one or more medical grade gases (e.g., oxygen, air, nitrous oxide, or combinations thereof), which may then be delivered to a patient.

Anesthesia machine 100 may additionally include an integrated suction, an auxiliary oxygen flow control, and various other components for providing and/or controlling a flow of the one or more medical grade gases to the patient. In the embodiment shown, anesthesia machine 100 includes one or more pipeline connections 146 to facilitate coupling of the anesthesia machine to pipeline gas sources. Additionally, anesthesia machine 100 includes a cylinder yoke 144, via which one or more gas-holding cylinders 148 may be coupled to the anesthesia machine. Thus, through the pipeline connection and/or cylinder connections, gas may be provided to the anesthesia machine, where the gas may include (but is not limited to) medical air, oxygen, nitrogen, and nitrous oxide. The gas that enters the anesthesia machine may mix with the vaporized anesthetic agent at the anesthetic vaporizer 114, as described above, before being supplied to a patient via the ventilator 112. The anesthesia machine may also include a serial port, a collection bottle connection, and a cylinder wrench storage area. Further, in some embodiments, the anesthesia machine may include an anesthesia gas scavenging system 132, as will be elaborated below with respect to FIG. 3.

The ventilator 112 may include an expiratory check valve at an expiratory port 120, an expiratory flow sensor at the expiratory port 120, an inspiratory check valve at an inspiratory port 118, an inspiratory flow sensor at the inspiratory port 118, an absorber canister, a manual bag port, a ventilator release, an adjustable pressure-limiting valve, a bag/vent switch, and a bellows assembly. When a patient breathing circuit is coupled to the ventilator 112, breathing gases (e.g., air, oxygen, and/or nitrous oxide mixed with vaporized anesthetic agent) exit the anesthesia machine from the inspiratory port 118 and travel to the patient. Expiratory gases from the patient re-enter the anesthesia machine via the expiratory port 120, where carbon dioxide may be removed from the expiratory gases via the absorber canister.

During operation of the anesthetic vaporizer 114, an operator (e.g., an anesthesiologist) may adjust an amount of vaporized anesthetic agent that is supplied to the patient by adjusting a flow rate of gases from the gas source(s) (e.g., the pipeline gas supply) to the vaporizer. The flow rate of the gases from the gas source to the vaporizer may be adjusted by the operator via adjustment of one or more flow adjustment devices. For example, the flow adjustment devices may include analog and/or digital adjustment dials and/or other user input devices configured to actuate one or more flow control valves of anesthesia machine 100. In some embodiments, a first flow control valve may be positioned between the gas source(s) and the anesthetic vaporizer 114 and may be actuatable via the flow adjustment devices to a fully opened position, a fully closed position, and a plurality of positions between the fully opened position and the fully closed position.

Anesthesia machine 100 may additionally include one or more valves configured to bypass gases from the gas source (s) around the anesthetic vaporizer 114. The valves may enable a first portion of gases to flow directly from the gas source to the inspiratory port 118 and a second portion of gases to flow from the gas source through the anesthetic vaporizer 114 to mix with the vaporized anesthetic agents prior to flowing to the inspiratory port 118. By adjusting a ratio of the first portion of gases relative to the second portion of gases, the operator may control a concentration of vaporized anesthetic agent administered to the patient via the inspiratory port 118.

Further, the adjustments described above may be facilitated at least in part based on output from the respiratory gas module 108. The respiratory gas module 108 may be configured to measure various parameters of the gases exiting the vaporizer and/or being provided to the patient. For example, the respiratory gas module 108 may measure the concentrations of carbon dioxide, nitrous oxide, and the anesthetic agent provided to the patient. Further, the respiratory gas module 108 may measure respiration rate, minimum alveolar concentration, patient oxygen, and/or other parameters. The output from the respiratory gas module 108 may be displayed via a graphical user interface on a display device (e.g., the anesthesia display device 104 and/or the patient monitoring display device 106) and/or used by a controller to provide closed-loop feedback control of the amount of anesthesia provided to the patient.

The ventilator 112 may optionally be coupled to a breathing circuit (not shown) including a plurality of tubes (e.g., gas passages) 122. The breathing circuit may be coupled between an airway of a patient (e.g., via a breathing mask positioned to enclose the mouth and/or nose of the patient or a tracheal intubation tube) and the inspiratory port 118. Gases (e.g., the one or more medical gases, or a mixture of the one or more medical gases and vaporized anesthetic agent from the anesthetic vaporizer 114) may flow from the inspiratory port 118, through the breathing circuit, and into the airway of the patient, where the gases are absorbed by the lungs of the patient. By adjusting the concentration of vaporized anesthetic agent in the gases as described above, the operator may adjust a degree to which the patient is anesthetized.

During conditions in which the breathing circuit is coupled to the airway, the anesthetic agent and/or fresh gas (without the anesthetic agent) may flow into the airway of the patient (e.g., through inhalation) via the inspiratory port 118 and the inspiratory check valve. As an example, the inspiratory check valve may open automatically (e.g., without input or adjustment by the operator) in response to inhalation by the patient and may close automatically in response to exhalation by the patient. Similarly, the expiratory check valve may open automatically in response to exhalation by the patient and may close automatically in response to inhalation by the patient.

In some embodiments, the operator may additionally or alternatively control one or more operating parameters of the anesthesia machine 100 via an electronic controller 140 of the anesthesia machine 100. Controller 140 includes a processor operatively connected to a memory. The memory may be a non-transitory computer-readable medium and may be configured to store computer executable code (e.g., instructions) to be processed by the processor in order to execute one or more routines, such as those described herein. The memory may also be configured to store data received by the processor. Controller 140 may be communicatively coupled (e.g., via wired or wireless connections) to one or more external or remote computing devices, such as a hospital computing system, and may be configured to send and receive various information, such as electronic medical record information, procedure information, and so forth. Controller 140 may also be electronically coupled to various other components of the anesthesia machine 100, such as the anesthetic vaporizer 114, the ventilator 112, the respiratory gas module 108, the anesthesia display device 104, and the patient monitoring display device 106.

The controller 140 receives signals from the various sensors of the anesthesia machine 100 and employs the various actuators of the anesthesia machine 100 to adjust operation of the anesthesia machine 100 based on the received signals and instructions stored on the memory of the controller. For example, the flow of gases to the inspiratory port 118 may be controlled via an input device (e.g., keyboard, touchscreen, etc.) coupled to the electronic controller of the anesthesia machine 100. The controller 140 may display operating parameters of the anesthesia machine 100 via the anesthesia display device 104 and/or the patient monitoring display device 106. The controller may receive signals (e.g., electrical signals) via the input device and may adjust operating parameters of the anesthesia machine 100 in response (e.g., responsive) to the received signals.

As one example, the operator may input a desired concentration of the anesthetic agent to be delivered to the patient. A corresponding valve position of one or more valves of the anesthesia machine (e.g., a position of one or more bypass valves, as described above) may be empirically determined and stored in a predetermined lookup table or function in a memory of the controller. For example, the controller may receive the desired concentration of the anesthetic agent via the input device and may determine an amount of opening of the one or more valves corresponding to the desired concentration of the anesthetic agent based on the lookup table, with the input being the concentration of the anesthetic agent and the output being the valve position of the one or more valves. The controller may transmit an electrical signal to an actuator of the one or more valves in order to adjust each of the one or more valves to the corresponding output valve position. In some examples, the controller may compare the desired flow rate of gases to a measured flow rate of gases, such as measured by the inspiratory flow sensor, for example.

Controller 140 is shown in FIG. 1 for illustrative purposes, and it is to be understood that controller 140 may be located in various locations within, around, and/or remote from anesthesia machine 100. As an example, controller 140 may include multiple devices/modules that may be distributed throughout anesthesia machine 100. As such, controller 140 may include a plurality of controllers at various locations within anesthesia machine 100. As another example, additionally or alternatively, controller 140 may include one or more devices/modules that are external to anesthesia machine 100, located proximate to (e.g., in a same room) or remote from (e.g., a remote server) anesthesia machine 100. In each example, the multiple devices/modules may be communicatively coupled through wired and/or wireless connections.

Anesthetic vaporizers, such as anesthetic vaporizer 114 shown in FIG. 1, may employ various methods to vaporize a liquid anesthetic agent. For example, the anesthetic vaporizer may use a flow-over method (in which a carrier gas flows over a top surface of a volatile liquid anesthetic agent), a bubble-through method (in which the carrier gas is bubbled up through the liquid anesthetic agent), or a gas/vapor blender (in which heat is used to vaporize the liquid anesthetic agent, and the vapors are injected into a fresh gas flow). Regardless of the vaporization method, in some embodiments, the anesthetic vaporizer 114 may include a refillable sump for storing the liquid anesthetic agent before it is delivered to a vaporizing chamber.

During routine refill events and during operation, WAGs may be emitted by the anesthetic vaporizer 114, which may decrease the air quality of a clinical and/or surgical environment. Further, internal leaks in anesthetic vaporizer 114 may release WAGs into the clinical and/or surgical environment. Therefore, FIGS. 2-5B provide embodiments for scavenging (e.g., sequestering) WAGs and/or alerting a user to the presence of WAGs.

FIG. 2 shows an exemplary embodiment of an anesthetic vaporizer 200, which may be included in an anesthesia machine (e.g., anesthesia machine 100 shown in FIG. 1). As one example, anesthetic vaporizer 200 may be anesthetic vaporizer 114 of FIG. 1. In the embodiment shown in FIG. 2, anesthetic vaporizer 200 is a bubble-through anesthetic vaporizer, including a vaporizing chamber 202 defined by a housing 204. However, in other embodiments, anesthetic vaporizer 200 may be another type of anesthetic vaporizer (e.g., flow-over, injector-based, wick-based, etc.) for use with a volatile liquid anesthetic agent.

A lower portion of vaporizing chamber 202 is shown holding a liquid anesthetic agent 210 that is supplied from a sump 222 via a conduit 214 and a pump 220. The liquid anesthetic agent 210 may be isoflurane, sevoflurane, or another liquid anesthetic agent of similar volatility, for example, that is stored in sump 222. Pump 220 may be a positive displacement pump, such as a reciprocating positive displacement pump, for example. Pump 220 may be selectively operated to deliver liquid anesthetic agent 210 from sump 222 to vaporizing chamber 202 in response to a command signal from a controller 225, as will be further described below. Controller 225 may be an electronic controller including a processor operatively connected to a memory 228. Controller 225 may be included in (e.g., a part of) or communicatively coupled to controller 140 shown in FIG. 1, for example.

Sump 222 may be refilled via a filler apparatus 232. Filler apparatus 232 includes a filler port 227 having an inlet filler port valve 229 positioned therein. In some embodiments, filler apparatus 232 may further include a fill cap (not shown in FIG. 2) configured to cover filler port 227 when a refilling event is not occurring. For example, an operator of anesthetic vaporizer 200 may remove the fill cap to refill sump 222 with additional liquid anesthetic agent 210 (e.g., from a refill bottle) via filler port 227 and inlet filler port valve 229 and then replace the fill cap to seal sump 222. The fill cap may be a screw cap, for example. In some embodiments, inlet filler port valve 229 may be a mechanically actuated spring-loaded valve that opens when the refill bottle is attached to filler port 227 to enable liquid anesthetic agent 210 to flow from the refill bottle to the interior of sump 222 and (fully) closes when the refill bottle is not attached to filler port 227. Additionally or alternatively, in some embodiments, inlet filler port valve 229 may be an electronically actuated valve that may be adjusted in response to a control signal received from controller 225, as will be further described below. Thus, in some embodiments, inlet filler port valve 229 may be both mechanically and electronically actuated, and the sump 222 may be a sealed system when the fill cap is in place and/or the filler port valve 229 is (fully) closed.

Further, in the exemplary embodiment shown in FIG. 2, filler apparatus 232 includes a sequestration channel 223 surrounding filler port 227 and coupled to a conduit 234. As will be elaborated below with respect to FIGS. 3-5A, conduit 234 may conduct suction (e.g., vacuum, or negative pressure with respect to atmospheric pressure) from a suction source to sequestration channel 223 in order to draw gases within the vicinity of filler apparatus 232 through sequestration channel 223. Thus, conduit 234 may serve as a suction inlet for sequestration channel 223, which may funnel the gases to conduit 234. The gases may include ambient air, anesthetic agent gases (e.g., WAGs), or a mixture of ambient air and anesthetic agent gases. In one embodiment, conduit 234 may draw the WAGs to an active scavenging system of the anesthesia machine, as will be described with respect to FIG. 3. In another embodiment, sequestration channel 223 may include a filter for adsorbing WAGs positioned therein, and thus, gases drawn through conduit 234 may be stripped of anesthetic gases after passing through the filter, as will be described with respect to FIGS. 4-5B. In both embodiments, WAGs produced through a refilling event at filler apparatus 232 are sequestered instead of diffusing throughout the ambient environment.

Further still, filler apparatus 232 may include one or more sensors 221 that may be used by controller 225 to determine when a refilling event is occurring. In some embodiments, the one or more sensors 221 may include a filler port occupancy sensor that outputs a signal to controller 225 indicative of a presence or absence of a refill bottle inserted into filler port 227. For example, the filler port occupancy sensor may be an optical, electromechanical, Hall effect, capacitive, strain gauge switch, or other type of sensor coupled to, within, or proximate to filler port 227. In some embodiments, the one or more sensors 221 may additionally or alternatively include a volatile organic compound (VOC) sensor coupled to, within, or proximate to filler port 227. Because liquid anesthetic agent 210 is a volatile organic solvent, anesthetic agent vapors (e.g., WAGs) are measurable by the VOC sensor. As will be elaborated herein, the VOC sensor may be configured to output a signal to controller 225 indicative of the presence or absence of WAGs in the vicinity of filler port 227. In some examples, the signal output by the VOC sensor may be used by controller 225 to determine an absolute or relative level (or concentration) of the WAGs, as will be further described below with particular respect to FIG. 6. Thus, sump 222 may be refilled via filler port 227 so that liquid anesthetic agent 210 is available for supply to vaporizing chamber 202 via conduit 214, and the one or more sensors 221 may be used to detect or infer a refilling event is occurring.

Conduit 214 may further include a shut-off valve 218 coupled between pump 220 and vaporizing chamber 202. For example, shut-off valve 218 may be an on-off valve, wherein shut-off valve 218 is actuated to an open (e.g., fully open) position that allows liquid anesthetic agent 210 to flow between and pump 220 and vaporizing chamber 202 or a closed (e.g., fully closed) position that prevents (e.g., blocks) the flow of liquid anesthetic agent 210 between pump 220 and vaporizing chamber 202. Shut-off valve 218 may be actuated between the open and closed positions in response to a command signal from controller 225, for example. A liquid return line 215 may be coupled to conduit 214 between shut-off valve 218 and pump 220 to reduce pressure build up between shut-off valve 218 and pump 220, such as when shut-off valve 218 is closed. For example, excess liquid anesthetic agent 210 provided by pump 220 may be returned to sump 222 via liquid return line 215. Further, liquid return line 215 may include a restriction 217, such as an orifice, to control flow through liquid return line 215 such that liquid anesthetic agent 210 preferentially flows through shut-off valve 218 instead of restriction 217 when shut-off valve 218 is open.

Controller 225 may selectively activate pump 220 to provide liquid anesthetic agent 210 from sump 222 to vaporizing chamber 202. In one embodiment, controller 225 may adjust operation of pump 220 responsive to a measurement received from a level sensor 224. For example, level sensor 224 may be any type of liquid level sensor, such as an optical, ultrasonic, capacitive, float, or pressure-based liquid level sensor positioned to measure a level of liquid anesthetic agent 210 in vaporizing chamber 202. As one example, controller 225 may be configured to maintain the level of liquid anesthetic agent at a target level or within a target range in order to prevent both underfilling and overfilling of vaporizing chamber 202.

In some embodiments, pump 220 may include a positive displacement stepper motor, where each positive displacement step of the pump is equivalent to a specified volume of liquid anesthetic agent 210. In this manner, the pump can be used to precisely fill the vaporizing chamber 202 and prevent overfilling by recording the number of pump steps delivered. This approach may also be used to record a volume of anesthetic agent delivered to vaporizing chamber 202, which may be used for vaporizer run-time/maintenance analysis (e.g., service metrics), liquid leak detection, precise determination of an amount of liquid anesthetic remaining and available for delivery, vaporization efficiency calculations, etc.

Conduit 214, shut-off valve 218, pump 220, and liquid return line 215 may all include seal sites that may potentially become degraded, resulting in an internal emission of WAGs. For example, conduit 214, shut-off valve 218, pump 220, and liquid return line 215 may be included in a pneumatic coupling system between sump 222 and vaporizing chamber 202. Therefore, in some embodiments, anesthetic vaporizer 200 may further include an internal VOC sensor positioned proximate to the pneumatic coupling system. As will be elaborated below with respect to FIGS. 3-4 and 6, the internal VOC sensor may provide a signal to controller 225 indicative of the presence or absence of WAGs internal to anesthetic vaporizer 200.

Anesthetic vaporizer 200 includes an additional level sensor 230 positioned to measure a level of liquid anesthetic agent 210 in sump 222. Level sensor 230 may be any type of liquid level sensor, such as an optical, ultrasonic, capacitive, float, or pressure-based liquid level sensor, for example. In the embodiment shown in FIG. 2, level sensor 230 includes an optical time-of-flight (ToF) proximity sensor. Further, controller 225 may track the level (or volume) of liquid anesthetic agent 210 in sump 222 before, during, and after refilling via measurements received from level sensor 230. In embodiments where inlet filler port valve 229 is electronically actuated, controller 225 may actuate inlet filler port valve 229 closed responsive to the measured level (or volume) reaching a maximum level (or volume) to prevent inadvertent overfilling/overflowing of sump 222.

An upper portion of vaporizing chamber 202 (e.g., above a surface of liquid anesthetic agent 210) holds vapor, which may be a mixture of vaporized anesthetic agent and a carrier gas from a fresh gas flow. The fresh gas flow, and thus the carrier gas, may include one or more medical grade gases, such as oxygen, air, nitrous oxide, and combinations thereof. The fresh gas flow may be provided via one or more gas pipelines (e.g., via pipeline connections 146 shown in FIG. 1) and/or one or more gas-holding cylinders (e.g., gas-holding cylinder 148 of FIG. 1). As shown in FIG. 2, the fresh gas flow may enter anesthetic vaporizer 200 via a first gas passage 236. A first mass flow sensor 241 may be coupled to first gas passage 236 to measure a flow rate of the fresh gas flow entering anesthetic vaporizer 200. For example, first mass flow sensor 241 may be an ultrasonic flow meter or a calorimetric (thermal) mass flow meter.

In the exemplary embodiment of FIG. 2, a second gas passage 238 branches off from first gas passage 236 downstream of first mass flow sensor 241 to provide carrier gas to vaporizing chamber 202. As used herein, "carrier gas" refers to a portion of the fresh gas flow that flows to vaporizing chamber 202, whereas "bypass gas" refers to a remaining portion of the fresh gas flow that does not flow through vaporizing chamber 202, as will be elaborated below. For example, second gas passage 238 may pass through an opening in housing 204, which may include a gas-tight seal, to flow the carrier gas through a bottom of vaporizing chamber 202. However, in other embodiments, anesthetic vaporizer 200 may not include second gas passage 238, and carrier gas may not be delivered to vaporizing chamber 202. For example, carrier gas may not be delivered to vaporizing chamber 202 when the liquid anesthetic agent 210 has a relatively low boiling point (e.g., at or around room temperature), such as when liquid anesthetic agent 210 is desflurane or another liquid anesthetic agent of similar volatility. Additionally or alternatively, second gas passage 238 may not be included in embodiments where a different type of anesthetic vaporizer architecture is used (e.g., a flow over type or a gas/vapor blender). Thus, the embodiment shown in FIG. 2 is provided by way of example.

The carrier gas delivered to vaporizing chamber 202 via second gas passage 238 flows through liquid anesthetic agent 210 to form a plurality of gas bubbles 212. The plurality of gas bubbles 212 pass through liquid anesthetic agent 210, becoming saturated with vaporized anesthetic agent, as they rise to the surface of the liquid. In some examples, a heating element may be coupled to or within vaporizing chamber 202 to increase a temperature of liquid anesthetic agent 210 and provide energy for vaporization (e.g., latent heat of vaporization).

Vapor, such as the carrier gas that is saturated with vaporized anesthetic agent, may flow out of vaporizing chamber 202 via a third gas passage 240 (e.g., a vapor delivery passage). For example, third gas passage 240 may pass through an opening at or near a top of housing 204 and form a junction with first gas passage 236 to fluidically couple the upper portion of vaporizing chamber 202 with first gas passage 236. Upstream of the junction with third gas passage 240 and downstream of the junction with second gas passage 238, first gas passage 236 carries the bypass gas portion of the fresh gas flow. The bypass gas does not pass through vaporizing chamber 202. The bypass gas, containing no vaporized anesthetic agent, and the vapor from vaporizing chamber 202, containing the carrier gas saturated with the vaporized anesthetic agent, mix at and downstream of the junction between first gas passage 236 and third gas passage 240. The mixed gas may then be delivered to the patient via an inspiratory limb of a breathing circuit (e.g., via inspiratory port 118 described with respect to FIG. 1).

A second mass flow sensor 244 may be coupled to first gas passage 236 downstream of the junction with third gas passage 240 to measure a flow rate of the mixed gas exiting anesthetic vaporizer 200. For example, second mass flow sensor 244 may be an ultrasonic flow meter or a calorimetric mass flow meter. In the example of an ultrasonic flow metering architecture, an anesthetic agent concentration may be calculated by the difference in the measured time-of-flight between upstream ultrasonic flow sensor 241 and downstream ultrasonic flow sensor 244. In some embodiments, an independent concentration sensor 256 may be coupled to first gas passage 236 downstream of the junction with third gas passage 240. Concentration sensor 256 may be any suitable sensor that is configured to measure a concentration of the anesthetic agent in the mixed gas. As one example, concentration sensor 256 may be an optical sensor that transmits light of a suitable wavelength (e.g., infrared) through the mixed gas and determines a concentration of the anesthetic agent based on an absorption of the light by the mixed gas. In other examples, the concentration sensor may be a carbon dioxide or oxygen sensor that measures the concentration of the anesthetic agent based on a displacement of the carbon dioxide or oxygen relative to a supplied concentration of carbon dioxide or oxygen in the fresh gas flow. Concentration sensor 256 may output a signal to controller 225 indicative of the measured concentration of the anesthetic agent (e.g., the concentration of the anesthetic agent vapor) in the mixed gas.

In addition to receiving signals output by the one or more sensors 221 included in filler apparatus 232, level sensor 224, level sensor 230, concentration sensor 256, first mass flow sensor 241, and second mass flow sensor 244, controller 225 may receive additional signals, including signals from one or more pressure, temperature, and VOC sensors coupled in various locations throughout anesthetic vaporizer 200. Controller 225 receives the signals from the various sensors of FIG. 2, processes the input data, and employs the various actuators of FIG. 2 to adjust operation of anesthetic vaporizer 200 based on the received signals and instructions stored on a memory of the controller. Additionally, the controller may output an alert to the operator via a human-machine interface (HMI) 226 that is operationally connected to the controller (e.g., via wired or wireless communication) responsive to a refill indication. Further, data may be input to controller 225 by the operator of anesthetic vaporizer 200 via HMI 226. Thus, HMI 226 may include both a user input device and an output device. The user input device may include one or more of a mouse, a keyboard, a voice input device, a touch input device for receiving a gesture from the operator, a motion input device for detecting non-touch gestures and other motions by the operator, and other comparable input devices, as well as associated processing elements capable of receiving user input from the operator. The output device may include one or more of a display (e.g., anesthesia display device 104 and/or patient monitoring display device 106 of FIG. 1) for providing visual alerts or text-based messages and a speaker for providing audible alerts or messages.

Turning now to FIG. 3, a first exemplary embodiment of a WAG scavenging system is shown. In particular, FIG. 3 shows a WAG scavenging system 300, which includes an anesthetic vaporizer 303 interfaced with an active scavenging system 302 of an anesthesia machine 301 to which it is mated. Anesthetic vaporizer 303 may be anesthetic vaporizer 200 of FIG. 2 and may include all or some of the components shown in FIG. 2. Therefore, components of anesthetic vaporizer 303 of FIG. 3 that are identical to components of anesthetic vaporizer 200 of FIG. 2 are numbered the same and will not be reintroduced. Further, some components of anesthetic vaporizer 303 may not be shown, although it may be understood that they may also be included in anesthetic vaporizer 303. Further still, anesthesia machine 301 may be anesthesia machine 100 of FIG. 1 and may include all or some of the components described with respect to FIG. 1. For example, active scavenging system 302 may be active scavenging system 132 of FIG. 1 and may draw in WAGs from the surrounding air via suction for processing and recirculation.

As shown in FIG. 3, anesthetic vaporizer 303 may be communicatively coupled to anesthesia machine 301 via a number of electrical contacts. Specifically, electrical contacts 304 of anesthetic vaporizer 303 are positioned on an exterior (e.g., external) housing 340 of anesthetic vaporizer 303 and electrically coupled to electrical contacts 306 of anesthesia machine 301. Electrical contacts 306 of anesthesia machine 301 and electrical contacts 304 of anesthetic vaporizer 303 may exchange electrical power and/or data. For example, anesthetic vaporizer 303 may transmit data such as sensed levels of VOCs (e.g., data from sensors such as sensors 221), vaporizer fill status (e.g., whether a refill event status is detected), liquid anesthetic levels, and notification messages to anesthesia machine 301. Similarly, anesthesia machine 301 may communicate various anesthesia settings and available connections to anesthetic vaporizer 303 (including the connection to active scavenging system 302, for example). In some embodiments, one or more pieces of data transmitted between anesthetic vaporizer 303 and anesthesia machine 301 may be displayed to a user via a human-machine interface (e.g., HMI 226 of FIG. 2), a voice notification, a sound notification, or a printed activity log. In other embodiments, data transmitted between anesthetic vaporizer 303 and anesthesia machine 301 may not be displayed to a user.

Anesthetic vaporizer 303 includes a filler apparatus 332, which is one exemplary embodiment of filler apparatus 232 of FIG. 2. Filler apparatus 332 includes a perforated disc 308, which includes a number of vent holes 310. Perforated disc 308 is positioned within sequestration channel 223 and adjacent to filler port 227. In some embodiments, such as the embodiment shown in FIG. 3, a surface at the outer circumference of perforated disc 308 is at least partially surrounded by and in direct contact with a surface at the inner circumference of sequestration channel 223 without any gaps. Similarly, a surface at the inner circumference of perforated disc 308 may be in direct contact with a surface at the outer circumference of filler port 227 without any gaps. Therefore, sequestration channel 223 may be fluidically coupled to the external environment surrounding filler apparatus 332 via vent holes 310, and suction may be applied through vent holes 310 when active scavenging of WAGs is desired. For example, a controller (e.g., controller 225 of FIG. 2) may determine that a refill event is occurring at filler port 227 based on output from the one or more sensors 221, which may trigger a request for active scavenging, as will be further described below with respect to FIG. 6. When suction is applied through vent holes 310, air (e.g., ambient air including WAGs in the vicinity of filler apparatus 332) may be pulled into sequestration channel 223, which may direct the air into conduit 234.

WAG scavenging system 300 includes conduit 234 fluidically coupled to active scavenging system 302 of anesthesia machine 301. In the embodiment shown, conduit 234 includes a vaporizer scavenging valve 312. Vaporizer scavenging valve 312 may be an on-off valve, wherein vaporizer scavenging valve 312 is actuated to an open (e.g., fully open) position that allows flow through vaporizer scavenging valve 312 and a closed (e.g., fully closed) position that prevents (e.g., blocks) flow through vaporizer scavenging valve 312. Vaporizer scavenging valve 312 may be actuated between the open and closed positions in response to a command signal from the controller, for example, in order to transmit or stop transmitting suction from active scavenging system 302 to sequestration channel 223. However, in other embodiments, vaporizer scavenging valve 312 may not be included, and flow through conduit 234 may be controlled via a scavenging valve 318 within anesthesia machine 301, as will be elaborated below.

Anesthetic vaporizer 303 includes a scavenging port 314 in exterior housing 340, through which the conduit 234 may traverse exterior housing 340 to exit anesthetic vaporizer 303. Similarly, anesthesia machine 301 includes a pneumatic connector 316 through which conduit 234 may enter anesthesia machine 301 to connect with active scavenging system 302. Pneumatic connector 316 may form a gas-tight seal around conduit 234, for example, such that captured gases flow out of anesthetic vaporizer 303 and into anesthesia machine 301 without any leaks. As such, when vaporizer scavenging valve 312 is open, captured gases may pass through vaporizer scavenging port 314 into anesthesia machine 301.

Scavenging valve 318 may be a master scavenging valve that controls whether active scavenging is shut on or shut off at anesthesia machine 301. Scavenging valve 318 may be an on-off valve, wherein scavenging valve 318 is actuated to an open (e.g., fully open) position that allows flow through vaporizer scavenging valve 312 and a closed (e.g., fully closed) position that prevents (e.g., blocks) flow through scavenging valve 318. Scavenging valve 318 may be actuated between the open and closed positions in response to a command signal from the controller, for example, in order to transmit or stop transmitting suction from active scavenging system 302 to sequestration channel 223. Thus, when scavenging valve 318 and vaporizer scavenging valve 312 are both in open positions, captured gases are pulled into the active scavenging system 302 of anesthesia machine 301. Active scavenging system 302 may include a filter, such as a carbon or activated charcoal filter, that is configured to adsorb WAGs as they are pulled through via suction.

Thus, the anesthetic vaporizer 303 is coupled to active scavenging system 302 of anesthesia machine 301 to mitigate the presence of WAGs in a clinical and/or surgical environment by actively drawing air (which may include WAGs) into the active scavenging system of the anesthesia machine. In some embodiments, the active scavenging process may be initiated responsive to a refill event and/or to vaporizer operation. In some embodiments, the one or more sensors 221 include a filler port occupancy sensor, and the filler port occupancy sensor may transmit a signal to the controller when the filler port is occupied, and the controller may determine that a refill event is occurring based on the signal from the filler port occupancy sensor. In some embodiments, the one or more sensors 221 include an inlet VOC sensor, which monitors VOC levels around filler apparatus 332. When a sensed VOC level exceeds a threshold level, the controller may determine that a refill event is occurring. In some examples, a user (e.g., an anesthesiologist or a technician) may command active scavenging during a refill event or during operation. Further, in some embodiments, the controller may compare the VOC level measured by the inlet VOC sensor to a measurement from a reference (e.g., ambient) VOC sensor 320 coupled to the exterior housing 340 at a position away from filler apparatus 332, as will be elaborated below with respect to FIG. 6. Because reference VOC sensor 320 is not proximate to filler apparatus 332, reference VOC sensor 320 may measure an ambient VOC level in the clinical and/or surgical environment. Further still, in some embodiments, the user may input the command via the HMI of anesthetic vaporizer 303 or via another input method (e.g., a button, a switch, or a selection wheel).

Further, in some examples, anesthetic vaporizer 303 may include one or more internal VOC sensors, such as an internal VOC sensor 322, which may monitor the air quality within the anesthetic vaporizer. Internal VOC sensor 322 may be placed near potential leak sites. In the embodiment shown in FIG. 3, internal VOC sensor 322 is positioned proximate to conduit 214, which is coupled between sump 222 and vaporizing chamber 202. A leak may occur if a connection between conduit 214 and sump 222 is not sufficiently tight, for example. In another example, a seal between conduit 214 and sump 222, between conduit 214 and vaporizing chamber 202, or between conduit 214 and another component (e.g., pump 220 or shut-off valve 218 shown in FIG. 2) may degrade overtime and may no longer be gas- or liquid-tight. In some embodiments, an output of internal VOC sensor 322 may be compared to the ambient VOC level measured by the reference VOC sensor 320. By comparing sensed levels of VOCs outside anesthetic vaporizer 303 with sensed levels of VOCs inside anesthetic vaporizer 303, the controller may determine that an internal leak has occurred, as will be elaborated below with respect to FIG. 6.

Continuing to FIG. 4, a second exemplary embodiment of a WAG scavenging system is shown. In particular, FIG. 4 shows a WAG scavenging system 400, which includes an anesthetic vaporizer 403 configured to independently sequester WAGs via a filter cartridge 402. Anesthetic vaporizer 403 may be anesthetic vaporizer 200 of FIG. 2 and may include all or some of the components shown in FIG. 2. Therefore, components of anesthetic vaporizer 403 of FIG. 4 that are identical to components of anesthetic vaporizer 200 of FIG. 2 are numbered the same and will not be reintroduced. Further, some components of anesthetic vaporizer 403 may not be shown, although it may be understood that they may also be included in anesthetic vaporizer 403.

Anesthetic vaporizer 403 is installed in an anesthesia machine 401, which may be anesthesia machine 100 of FIG. 1 and may include all or some of the components described with respect to FIG. 1. In the embodiment shown in FIG. 4, anesthesia machine 401 does not include an active scavenging system. Anesthetic vaporizer 403 may be communicatively coupled to anesthesia machine 401 via a number of electrical contacts. Specifically, electrical contacts 404 of anesthetic vaporizer 403 are positioned on an exterior (e.g., external) housing 440 of anesthetic vaporizer 403 and electrically coupled to electrical contacts 406 of anesthesia machine 401. Electrical contacts 404 of anesthetic vaporizer 403 and electrical contacts 406 of anesthesia machine 401 may function the same as electrical contacts 304 and electrical contacts 306 described with respect to FIG. 3, for example.

In the embodiment shown, filter cartridge 402 is included in a filler apparatus 432, which may be one exemplary embodiment of filler apparatus 232 introduced in FIG. 2. Filter cartridge 402 may be comprised of activated charcoal or carbon enclosed within a porous casing. Additionally or alternatively, filter cartridge 402 may include a functionalized resin configured to bind WAGs and/or any other WAG adsorbent material. In the embodiment shown in FIG. 4, filter cartridge 402 is a ring-shaped disc sized to fit into a recessed portion of sequestration channel 223 such that air flowing into sequestration channel 223 passes through filter cartridge 402, as will be described in more detail with respect to FIGS. 5A-5B. In other embodiments, filter cartridge 402 may be positioned in other locations fluidically coupled to sequestration channel 223, such as within conduit 234, so that air that flows through sequestration channel 223 may also pass through filter cartridge 402. Filter cartridge 402 may be a removable and replaceable unit, as will be elaborated below.

When WAG sequestration is requested (e.g., based on data from the one or more sensors 221), suction may be applied to filter cartridge 402 by a suctioner. In the exemplary embodiment of WAG scavenging system 400, the suctioner is a fan (or blower) 408, although other types of suctioners are also possible. Fan 408 may be positioned within exterior housing 440 such that a fan inlet 410 is fluidically coupled to sequestration channel 223 via conduit 234 and may blow air out of anesthetic vaporizer 403 through a fan outlet 412. In some embodiments, fan 408 is an axial flow fan, and an air flow may pass through fan 408 axially. In other embodiments, fan 408 is a centrifugal blower and may draw air in a circular path around the fan before expelling air from anesthetic vaporizer 403. Further, in some embodiments, fan 408 is a dedicated component of WAG scavenging system 400 that is only used for WAG sequestration, while in other embodiments, fan 408 is a multi-functional component that is also used during nominal anesthetic vaporizer operation (e.g., for cooling). Further still, in some embodiments Fan 408 may include rotating blades and/or a rotating impeller to produce a current of air by creating a pressure differential between fan inlet 410 and fan outlet 412. When fan 408 operates, suction created by the rotating blades and/or the rotating impeller draws surrounding air (e.g., ambient air including WAGs) through filter cartridge 402, sequestration channel 223, and conduit 234. As the WAGs are pulled through filter cartridge 402, they may adsorb to the adsorbent. Filter cartridge 402 may sequester at least a percentage of the WAGs, removing them from the air flow, and filtered air may flow from conduit 234 fan inlet 410 of fan 408. Fan outlet 412 may exhaust the filtered air to the exterior of anesthetic vaporizer 403 via holes or grating in exterior housing 440, for example. Thus, the anesthetic vaporizer 403 mitigates the presence of WAGs in a clinical and/or surgical environment by actively drawing air (e.g., air which may include WAGs) through a filter included in the anesthetic vaporizer itself, which sequesters VOCs (such as WAGs) before recirculating the filtered air to the clinical and/or surgical environment.

In some embodiments, an outlet VOC sensor 414 may monitor a level of WAGs in the filtered air leaving fan outlet 412. For example, when the level of WAGs in the filtered air leaving fan outlet 412 increases above a threshold, it may be determined that filter cartridge 402 is saturated and ready for replacement. However, in other embodiments, outlet VOC sensor 414 may not be included, and a controller (e.g., controller 225 of FIG. 2) may infer a replacement status based on, for example, a tracked usage of filter cartridge 402, as will be elaborated below with respect to FIG. 7. In some embodiments, filter cartridge 402 may be discarded and replaced with another filter cartridge of similar dimensions. In embodiments where filter cartridge 402 is comprised of activated charcoal/carbon, filter cartridge 402 may be regenerated (e.g., reactivated), such as through thermal processing. The thermal processing may remove and destroy the adsorbed WAGs, leaving a regenerated carbon-based adsorbent that can be reused. For example, the activated charcoal may be slowly heated in a kiln to high temperatures (e.g., 700-900° C.). During heating, impurities (e.g., the WAGs) may be desorbed from the charcoal and destroyed by a thermal oxidizer. After such a treatment, the filter cartridge may be replaced in the filler apparatus 432. Regenerating filter cartridges rather than discarding them may decrease the waste product of a medical facility and may decrease the production costs associated with fabricating new filter cartridges.

Anesthetic vaporizer 403 may further include an exterior reference VOC sensor 420 coupled to exterior housing 440 and an internal VOC sensor 422 positioned near pneumatic couplings between sump 222 and vaporizing chamber 202. Reference VOC sensor 420 may function similarly to reference VOC sensor 320 of FIG. 3, and internal VOC sensor 422 may function similarly to internal VOC sensor 322 of FIG. 3, for example.

Figure 5B:
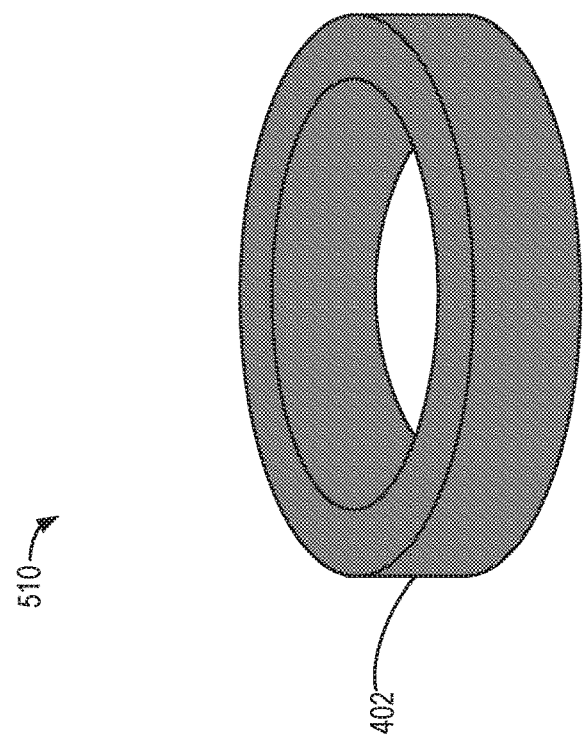
FIG. 5B shows a view of the sequestration filter cartridge of FIG. 5A.
Figure 5A:
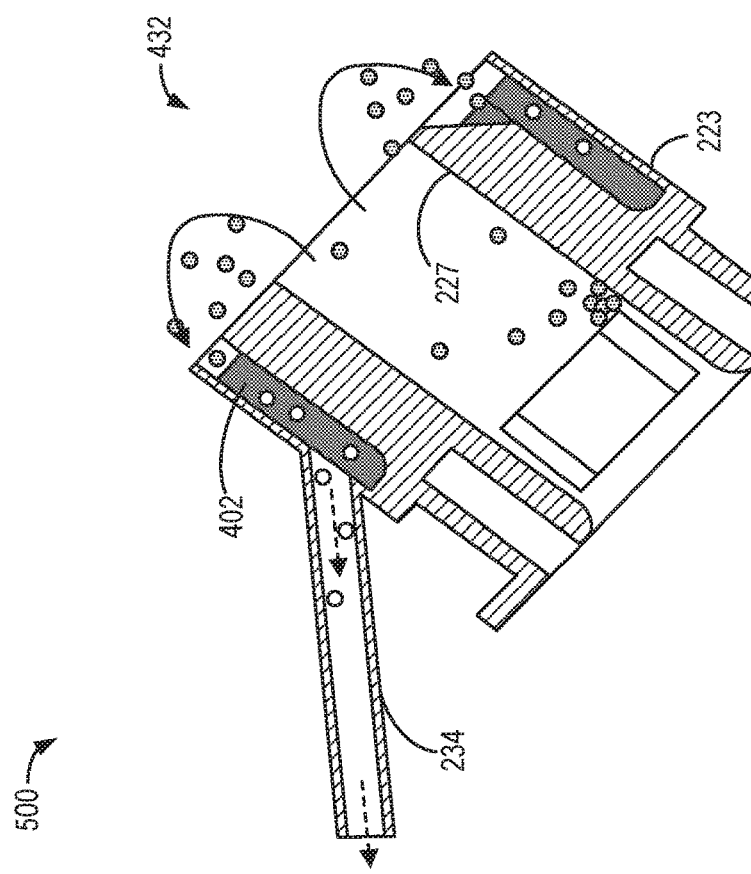
FIG. 5A shows a cross-sectional view of an exemplary embodiment of a sequestration filter cartridge included in a filler apparatus of an anesthetic vaporizer.

Continuing to FIGS. 5A and 5B, a cross-sectional view 500 of an exemplary embodiment of filler apparatus 432 introduced in FIG. 4 is shown in FIG. 5A, and a perspective view 510 of filter cartridge 402 introduced in FIG. 4 is shown in 5B. Therefore, components of FIGS. 5A and 5B that are identical to components of filler apparatus 432 of FIG. 4 are numbered the same and will not be reintroduced. Specifically, FIG. 5A shows filter cartridge 402 fitted into a recessed portion of sequestration channel 223. The recessed portion of sequestration channel 223 includes a tube encircling filler port 227 (only a portion of which is shown), which may couple to refill bottles to receive liquid anesthetic agent during refill events. In the embodiment shown in FIG. 5A, filter cartridge 402 is in direct contact with an inner wall (e.g., an inner circumference) of sequestration channel 223 and an outer wall (e.g., an outer circumference) of filler port 227. As particularly shown in FIG. 5B, filter cartridge 402 may be disc-shaped, having a hollow cylindrical interior that is shaped to fit around filler port 227 without any gaps between filler port 227 and filter cartridge 402. Further, filter cartridge 402 may not block access to filler port 227.

Conduit 234 is fluidically connected to sequestration channel 223 and to filter cartridge 402 such that gases entering sequestration channel 223 may flow into conduit 234 when suction is applied. The suction applied via conduit 234 draws a gaseous mixture of air and WAGs generated by a refilling event (represented by shaded circles) out of filler port 227 and the surrounding area and through the porous openings in filter cartridge 402. As the WAGs pass through filter cartridge 402, the WAGs are adsorbed to the adsorbent material of the filter cartridge, and filtered air free of WAGs (represented by open circles) exits sequestration channel 223 via conduit 234.

As mentioned with respect to FIG. 4, in some embodiments, the adsorbent material of filter cartridge 402 includes charcoal, which refers to an activated form of carbon. Further, the adsorbent material may include a plurality of small pores, which may increase a surface area of the adsorbent material. The large surface area of the adsorbent material may encourage WAG adsorption, and in some examples, additional surface treatments (e.g., functionalization) may further encourage WAG adsorption. In some embodiments, the activated charcoal may be fabricated from activated coal (e.g., activated carbon derived from coal). Further, in some embodiments, the disc may include additional structures, such as a plastic or metal shell to increase a structural stability of the disc, as well as a porous casing that encloses the adsorbent material without blocking gas flow through the adsorbent material.

The disc shown in FIGS. 5A and 5B is only one possible configuration for filter cartridge 402. In some embodiments, filter cartridge 402 may have a different shape, size, and/or dimension. In some embodiments, filter cartridge 402 may be thinner or thicker than shown in FIG. 5B. Further, in some embodiments, the disc may not be symmetrical about a central axis but may have a varying thickness across the disc. In some embodiments, filter cartridge 402 may not be disc-shaped or may not be positioned within sequestration channel 223 (but may still be fluidically coupled between sequestration channel 223 and the suction source).

Turning now to FIG. 6, a high-level flow chart of an example method 600 for detecting a presence of WAGs emitted by an anesthetic vaporizer of an anesthesia machine is shown. The anesthetic vaporizer may include various systems for sequestering WAGs generated during refilling, such as via a connection to an active scavenging system of the anesthesia machine (e.g., as described with respect to WAG scavenging system 300 of FIG. 3) or via a sequestration filter cartridge included in the anesthetic vaporizer (e.g., as described with respect to WAG scavenging system 400 of FIG. 4). Method 600 and the rest of the methods included herein may be executed by a controller, such as controller 225 of FIG. 2, according to instructions stored in a memory of the controller (e.g., memory 228 of FIG. 2) and in conjunction with one or more inputs, such as inputs received from an operator via a human-machine interface (e.g., HMI 226 of FIG. 2) and one or more sensors (e.g., the one or more sensors 221 of FIGS. 2-4, reference VOC sensor 320 of FIG. 3 or reference VOC sensor 420 of FIG. 4, and internal VOC sensor 322 of FIG. 3 or internal VOC sensor 422 of FIG. 4). Further, the controller may output information to the operator of the anesthesia machine via the human-machine interface.

At 602, the anesthetic vaporizer is monitored for WAG emissions. Monitoring for WAG emissions may include monitoring the anesthetic vaporizer for both internal WAG emissions and external WAG emissions. In some embodiments, monitoring the anesthetic vaporizer for WAG emissions may include inferring external WAG emissions due to a refilling event. Therefore, a filling status of a filler port may be monitored. In some embodiments, monitoring the anesthetic vaporizer for WAG emissions may additionally or alternatively include actively measuring VOC levels at one or more locations within or around the anesthetic vaporizer. For example, the one or more locations may include the filler port (e.g., via a filler port VOC sensor) positioned on the exterior of the anesthetic vaporizer and/or an internal location proximate to a pump and a vaporizing chamber (e.g., via the internal VOC sensor). While the filler port VOC sensor may measure WAGs present at or near the filler port (which may be emitted during a refilling event, for example), the internal VOC sensor may measure WAGs emitted within the anesthetic vaporizer due to leaks at internal vaporizer components (e.g., a pump, fluid and gas passage couplings, valve sites). In some examples, the one or more locations may further include an external location positioned away from the filler port that provides an ambient reference for comparative VOC measurements (e.g., the reference VOC sensor), as will be elaborated below.

At 604, it is determined if WAG emissions are detected. The WAG emissions may be detected external to the anesthetic vaporizer, internal to the anesthetic vaporizer, or both. In some embodiments, the occurrence of a refill event may be used to detect external WAG emissions. For example, it may be determined that a refilling event is occurring responsive to a signal from a filler port occupancy sensor indicating that a refill bottle is inserted in the filler port. In some embodiments, a refill event may be determined responsive to a signal from the filler port VOC sensor detecting the presence of WAGs. In other embodiments, the user may manually indicate a refilling event via the human machine interface, such as by selecting a "Fill Vaporizer" icon. As such, in some embodiments, the external emission of WAGs may be inferred based on an indication of a refilling event without a direct measurement.

In some embodiments, whether or not a refilling event is occurring, the detection of the WAG emissions may be determined with respect to the ambient VOC sensor, such as responsive to a VOC level measured by the filler port VOC sensor exceeding a VOC level measured by the reference VOC sensor by at least a threshold amount. In some embodiments, the detection of internal WAG emissions may be determined responsive to a VOC level measured by the internal VOC sensor exceeding a VOC level measured by the reference VOC sensor exceeding a VOC level measured by the reference VOC sensor by at least the threshold amount. Alternatively, the identification of the WAG emission may be performed without output from the reference VOC sensor, such as responsive to the VOC level measured by the filler port VOC sensor or the internal VOC sensor exceeding a pre-determined threshold level, the VOC level measured by the filler port VOC sensor and/or the internal VOC sensor increasing by at least the threshold amount within a threshold duration, etc. The threshold amount, the threshold level, and the threshold duration may each include a non-zero value that is calibrated to distinguish sensor noise from positive VOC detection.

If WAG emissions are not detected, method 600 proceeds to 606, and WAG emission monitoring is continued. This may include monitoring sensed levels of VOCs, as measured by the one or more VOC sensors described above. Additionally or alternatively, method 600 at 606 may include monitoring for an indication of a refilling event. Following 606, method 600 ends. For example, method 600 may be repeated at a pre-determined frequency.

If WAG emissions are detected at 604, method 600 proceeds to 608, and it is determined if WAG scavenging is indicated. In one embodiment, determining whether WAG scavenging is indicated may be based on whether the detected WAG emission is internal or external. For example, WAG scavenging may be indicated when the detected WAG emission is external, but not when the detected WAG emission is internal. In another embodiment, WAG scavenging may be indicated both when the detected WAG emission is external and when the detected WAG emission is internal, particularly because the WAGs released by the internal vaporizer components may diffuse into the surrounding environment over time, decreasing air quality in the vicinity of the anesthesia machine. In some embodiments, whether WAG scavenging is indicated may also be based on one or more user inputs. For example, a user may select between a setting to perform WAG scavenging only when the detected WAG emission is external and a setting to perform WAG scavenging whether the detected WAG emission is internal or external.

If WAG scavenging is not indicated at 608, method 600 proceeds to 610, and it is indicated that WAG emissions are detected. The indicating may include recording the emissions in a service log, as indicated at 612. For example, the service log may be a record of functions performed by and diagnostics performed on the anesthetic vaporizer that is stored in the memory of the controller. The service log may be accessible by the user of the anesthetic vaporizer and/or a service technician, such as via the HMI, for example. In some embodiments, the indication may include an indication that the emission of WAGs is occurring, a location at which the emission is occurring (e.g., internal and/or external), as well as the measured VOC level. Further, the indication may be time-stamped with date and time information to identify when the WAG emission was detected.

Further still, a maintenance alert may be output to the operator of the anesthetic vapor, as indicated at 614. For example, the controller may communicate the maintenance alert to the operator via the HMI. In some embodiments, the maintenance alert may include an audible alarm or message. In some embodiments, the maintenance alert may additionally or alternatively include a visual message. The message may include information regarding the WAG emissions (such as that WAG emissions have been detected) as well as a level determined from the VOC sensor measurement. Method 600 may then end. In some embodiments, method 600 may be repeated at a pre-determined frequency while the anesthetic vaporizer is powered "on" in order to continue checking for WAG emissions. As such, if internal WAG emissions coincide with some anesthetic vaporizer functions and not others (e.g., only during pumping), additional information may be provided to the user/service technician to infer a potential leakage site(s). As such, the service log of WAG emissions may help guide repair of the leakage site(s) in order to expedite the repair procedure and reduce an amount of time the anesthetic vaporizer is disabled.

Returning to 608, if WAG scavenging is indicated, method 600 proceeds to 616 and includes scavenging the WAGs by applying suction to a sequestration channel of a filler apparatus of the anesthetic vaporizer, as will be described below with respect to FIG. 7. In one embodiment, the sequestration channel of the anesthetic vaporizer may be fluidically coupled to an active scavenging system of the anesthesia machine, such that air drawn in to the sequestration channel is directed to the active scavenging system of the anesthesia machine for filtering. In another embodiment, applying suction to the sequestration channel may draw ambient air and WAGs through a filter cartridge positioned in the sequestration channel, which may remove WAGs from the air flow. In some embodiments, the method at 616 may also include recording the WAG emissions in the service log, as described above at 612. Thus, the emission detection may be recorded whether or not active WAG scavenging is indicated. Method 600 may then end.

Continuing to FIG. 7, a flow chart of an example method 700 for scavenging WAGs emitted by an anesthetic vaporizer included in an anesthesia machine is shown. The anesthetic vaporizer may include various systems for sequestering WAGs generated during refilling via a sequestration channel included in a filler apparatus (e.g., sequestration channel 233 described with respect to FIGS. 2-4). In some embodiments, method 700 may be performed by a controller (e.g., controller 225 of FIG. 2) as a part of method 600 of FIG. 6 (e.g., at 616). In some embodiments, additionally or alternatively, method 700 may be executed responsive to a user request for scavenging (e.g., via a human-machine interface, such as HMI 226 shown in FIG. 2).

At 702, a request for scavenging is received. As mentioned above, the request for scavenging may be responsive to a detection of WAG emissions (e.g., external WAG emissions and/or internal WAG emissions). Additionally or alternatively, the scavenging may be requested by the user of the anesthetic vaporizer, such as by activating a scavenging option.

At 704, it is determined if the anesthetic vaporizer has an active scavenging connection with the anesthesia machine. The active scavenging connection with the anesthesia machine may include the anesthetic vaporizer having a connection to the scavenging system of the anesthesia machine to which it is mated, as described with respect to FIG. 3. In some embodiments, the controller may automatically determine that the anesthetic vaporizer has the active scavenging connection with the anesthesia machine based on known anesthetic vaporizer components (e.g., whether or not an active scavenging hookup is included), preprogrammed instructions stored into the memory of the controller, or input from the user via selection of an appropriate setting via the HMI. For example, the user may select between an "active scavenging connection" option and a "no active scavenging connection" option when installing the anesthetic vaporizer in the anesthesia machine. Therefore, in some embodiments, the method may proceed directly from 702 to either 706 or 714 (as described further below) based on the preprogrammed instructions, known anesthetic vaporizer components, and/or the manual user selection. In some embodiments, the controller may additionally or alternatively receive information from the anesthesia machine to which it is mated (e.g., via electrical connections) regarding whether the anesthetic vaporizer is connected to its anesthesia gas scavenging system, whether or not it has an anesthesia gas scavenging system, etc.

If it is determined that the anesthetic vaporizer has an active scavenging connection with the anesthesia machine, method 700 proceeds to 706, and WAGs are scavenged via the active scavenging connection. In some embodiments, if the active scavenging system of the anesthesia machine is not already being operated to produce suction, the controller (or a controller of the anesthesia machine) may operate the active scavenging system to produce suction. In some embodiments, additionally or alternatively, an amount of suction produced by the active scavenging system may be increased.

At 708, one or more scavenging valves are opened to apply suction from the active scavenging system to the sequestration channel. The one or more scavenging valves include any or all valves disposed within a conduit fluidically coupling the sequestration channel to the active scavenging system (e.g., the suction source), such as a (first) scavenging valve included in the anesthetic vaporizer (e.g., vaporizer scavenging valve 312 of FIG. 3) and/or a (second) scavenging valve positioned within the anesthesia machine (e.g., scavenging valve 318 of FIG. 3). The controller may fully open the one or more scavenging valves in order to conduct suction from the active scavenging system to the sequestration channel to draw gases, including a mixture of ambient air and WAGs, into the sequestration channel, through the conduit, and to the active scavenging system, where the WAGs may be adsorbed or otherwise sequestered.

At 710, it is determined whether WAG scavenging is complete. In some embodiments, WAG scavenging may be determined to be complete when sensed levels of VOCs, a determined by a VOC sensor, are below a pre-determined first threshold. The pre-determined first threshold may be a non-zero VOC value or relative value (e.g., relative to a VOC level measured by a reference VOC sensor) that distinguishes WAG emissions from sensor noise, for example. In other embodiments, WAG scavenging may be determined to be complete when a refill event is no longer in progress, for example, based on an output from a fill port occupancy sensor. In some embodiments, the WAG scavenging may be considered to be complete a pre-determined duration after the fill port occupancy sensor detects removal of a refill bottle in order to continue scavenging WAGs generated while the refill bottle is removed.

If WAG scavenging is not determined to be complete, method 700 returns to 708, and the application of suction from the active scavenging system to the sequestration channel is continued. Thus, gases may continue to be drawn from around the filler apparatus and transported to the active scavenging system. If WAG scavenging is determined to be complete, method 700 proceeds to 712, and the one or more scavenging valves are closed. That is, any and all scavenging valves disposed in the conduit coupling the sequestration channel to the active scavenging system are fully closed, thus closing the active scavenging connection between the anesthetic vaporizer and the anesthesia machine. Method 700 may then end.

Returning to 704, if it is determined that the anesthetic vaporizer does not have an active scavenging connection with the anesthesia machine, method 700 proceeds to 714, and WAGs are scavenged via a sequestration filter cartridge included in the anesthetic vaporizer. That is, the anesthetic vaporizer may instead include a WAG sequestration system that is independent from the anesthesia machine, as described with respect to FIGS. 4-5B. In some embodiments, the sequestration filter cartridge may be positioned within the sequestration channel, such as filter cartridge 402 shown in FIGS. 4-5B. In other embodiments, the sequestration filter cartridge may be positioned in other locations fluidically coupled to the sequestration channel in order to filter WAGs drawn through the sequestration channel.

At 716, a blower or fan of the anesthetic vaporizer is operated at an increased speed to generate increased suction at the sequestration channel. An inlet of the blower or fan (e.g., fan 408 of FIG. 4) is fluidically coupled to the sequestration via a conduit so that suction (e.g., negative pressure) is conveyed to the sequestration channel from the blower or fan. In some embodiments, the speed of the blower or fan may be increased from zero responsive to the scavenging request. In some embodiments, the speed of the blower fan may be increased from a lower non-zero speed, such as when the blower or fan is already operating to provide cooling for the anesthetic vaporizer. In some embodiments, the speed of the blower or fan is increased to a maximum operating speed, while in other embodiments, the speed of the blower or fan is increased to a non-maximum, higher operating speed. Further, in some embodiments, the increased speed may be a pre-determined speed for creating a desired amount of suction (e.g., vacuum) at the sequestration channel. The suction draws gases, including a mixture of ambient air and WAGs, into the sequestration channel and through the sequestration filter cartridge, where the WAGs may be adsorbed or otherwise sequestered. The filtered gases may then pass through the blower or fan before being exhausted to the anesthetic vaporizer surroundings.

At 718, it is determined whether WAG scavenging is complete, as described above at 710. If WAG scavenging is not determined to be complete at 718, method 700 returns to 716, and the blower or fan continues to be operated at an increased speed to generate increased suction at the sequestration channel. Thus, emitted WAGs, particularly externally emitted WAGs, may continue to be sequestered. If instead WAG scavenging is determined to be complete, method 700 proceeds to 720, and the blower or fan is returned to a nominal operating speed for a current anesthetic vaporizer status. For example, the nominal operating speed for the blower or fan may be a pre-determined, non-zero value stored in the memory of the controller or may be determined based on operating conditions of the anesthetic vaporizer. As an example, the controller may input the operating conditions, such as an internal temperature of the anesthetic vaporizer, into a look-up table or map stored in memory, which may output the operating speed for the blower or fan for the input internal temperature.

At 722, it is determined whether the sequestration cartridge filter is saturated. In some embodiments, the anesthetic vaporizer may include an outlet VOC sensor positioned at an outlet of the blower or fan and configured to measure a level of VOCs (e.g., WAGs) exiting the blower or fan. For example, when the level of WAGs in the filtered gases leaving the blower or fan increases above a second threshold level, it may be determined that filter cartridge 402 is saturated and ready for replacement. In some embodiments, the second threshold level may be the same as the first threshold level described above at 710. In other embodiments, the second threshold level may be less than the first threshold level. Further, in some embodiments, the level of WAGs detected in the filtered gases leaving the blower or fan may be compared to the VOC level measured by the reference VOC sensor. However, in other embodiments, the outlet VOC sensor may not be included, and the controller may determine whether the sequestration cartridge filter is saturated based on a tracked usage of the sequestration cartridge filter. For example, the controller may calculate an amount of time that scavenging has been requested since a last filter cartridge replacement, which may be recorded in a service log. Once the amount of time reaches a pre-determined threshold duration, the controller may infer that the sequestration cartridge is saturated. The pre-determined threshold duration may be a time duration stored in memory that is calibrated based on average WAG emissions amounts and an estimated capacity of the sequestration filter cartridge, for example.

If the sequestration filter cartridge is determined to be saturated, method 700 proceeds to 724, and an alert to replace and/or regenerate the sequestration cartridge filter is output. In some embodiments, the alert may be communicated to the operator, such as via an icon or text-based message on the HMI. In some embodiments, the alert may additionally or alternatively include an audible alarm or message. In some embodiments, the controller may interface with another device (e.g., a computer or portable electronic device connected to controller via wired and/or wireless communication) to communicate the alert message to the user. Method 700 may then end.

If the sequestration cartridge filter is determined to be not saturated, method 700 proceeds to 726, and sequestration cartridge filter usage tracking is continued. In one embodiment, the controller may store the difference between the inlet VOC levels and the outlet VOC levels during each WAG scavenging event and may monitor these differences over time. In another embodiment, the controller may continue to track an amount of time during which active scavenging is requested. Method 700 may then end.

Thus, the methods and systems described herein provide for detecting waste anesthetic gas emissions from an anesthetic vaporizer and sequestering the emissions via a scavenging system that uses suction to draw the waste anesthetic gas emissions through an adsorbent filter. As a result, an air quality in the environment surrounding the anesthetic vaporizer, such as in a surgical suite or other medical facility, may be increased. Further, inadvertent exposure of medical professionals to the waste anesthetic gases may be decreased. Further still, silent leaks within the anesthetic vaporizer may be determined, enabling maintenance of the anesthetic vaporizer to be prompted.

A technical effect of using suction to draw waste anesthetic gases released by an anesthetic vaporizer through an adsorbent filter is that a level of the waste anesthetic gases in ambient air of a healthcare facility is decreased, thereby increasing an air quality of the healthcare facility.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

I claim:

1. A method for an anesthetic vaporizer installed in an anesthesia machine, comprising:
   detecting an emission of waste anesthetic gases (WAGs) from the anesthetic vaporizer; and
   responsive to detecting the emission of WAGs, performing at least one of scavenging the WAGs and outputting an alert,
   wherein scavenging the WAGs is responsive to detecting the emission of WAGs external to the anesthetic vaporizer and includes applying suction to a sequestration channel included in a filler apparatus of the anesthetic vaporizer, and
   wherein detecting the emission of WAGs external to the anesthetic vaporizer includes a level of WAGs measured by a volatile organic compound (VOC) sensor positioned on an exterior of the anesthetic vaporizer being greater than a threshold.

2. The method of claim 1, wherein detecting the emission of WAGs external to the anesthetic vaporizer includes a sensor coupled to the filler apparatus of the anesthetic vaporizer detecting a refill bottle is inserted in the filler apparatus.

3. The method of claim 1, wherein applying suction to the sequestration channel includes applying suction from an active scavenging system of the anesthesia machine, the active scavenging system of the anesthesia machine including a filter for adsorbing WAGs, and scavenging the WAGs further includes:
   opening one or more valves disposed in a suction inlet that fluidically couples the sequestration channel to the active scavenging system to conduct the suction from the active scavenging system to the sequestration channel via the suction inlet;
   drawing the WAGs through the sequestration channel and to the filter using the suction from the active scavenging system conducted to the sequestration channel via the suction inlet; and
   closing the one or more valves responsive to no longer detecting the emission of WAGs external to the anesthetic vaporizer.

4. The method of claim 1, wherein applying suction to the sequestration channel includes:
   operating a fan of the anesthetic vaporizer at an increased speed to generate suction at the fan, the suction at the fan conducted to the sequestration channel via a suction inlet that fluidically couples the sequestration channel to the fan;
   drawing the WAGs through the sequestration channel and through an adsorbent filter using the suction from the fan conducted to the sequestration channel via the suction inlet; and
   returning the fan to a nominal operating speed responsive to no longer detecting the emission of WAGs external to the anesthetic vaporizer.

5. The method of claim 4, wherein the adsorbent filter comprises a removable cartridge positioned within the sequestration channel.

6. The method of claim 4, further comprising:
   determining whether the adsorbent filter is saturated with WAGs based on at least one of an output of a second VOC sensor positioned at an outlet of the fan and a tracked usage of the adsorbent cartridge filter; and
   responsive to determining that the adsorbent filter is saturated with WAGs, outputting the alert, the alert including instructions to replace the adsorbent filter.

7. The method of claim 1, wherein outputting the alert is responsive to detecting the emission of WAGs internal to the anesthetic vaporizer, and the alert includes a maintenance alert.

8. The method of claim 7, wherein detecting the emission of WAGs internal to the anesthetic vaporizer includes a level of WAGs measured by a VOC sensor positioned within the anesthetic vaporizer being greater than a threshold.

9. A system for an anesthetic vaporizer, comprising:
   a sump configured to store liquid anesthetic agent, the sump positioned within an external housing of the anesthetic vaporizer;
   a filler apparatus coupled to the sump and positioned outside of the external housing, the filler apparatus including a filler port configured to receive a refill bottle of the liquid anesthetic agent and a sequestration channel coupled around the filler port;
   a conduit coupled between the sequestration channel and a suction source; and
   a controller storing executable instructions in non-transitory memory that, when executed, cause the controller to:
     identify an emission of waste anesthetic gases (WAGs) from the anesthetic vaporizer; and
     responsive to identifying the emission of WAGs, perform at least one of outputting an alert and scavenging the WAGs by applying suction from the suction source to the sequestration channel via the conduit,
   wherein the filler apparatus further includes at least one of a volatile organic compound (VOC) sensor and a filler occupancy sensor, and identifying the emission of WAGs external to the anesthetic vaporizer is based on output received from at least one of the VOC sensor and the filler occupancy sensor.

10. The system of claim 9, further comprising a VOC sensor coupled internal to the external housing of the anesthetic vaporizer, and wherein identifying the emissions of WAGs internal to the anesthetic vaporizer is based on output received from the VOC sensor.

11. The system of claim 9, wherein the suction source includes a blower positioned within the external housing, the system further comprises a filter cartridge positioned within the sequestration channel and adjacent to the filler port, and the instructions that cause the controller to perform at least one of outputting the alert and scavenging the WAGs by applying suction from the suction source to the sequestration channel via the conduit include further instructions stored in non-transitory memory that, when executed, cause the controller to:
  operate the blower fan at an increased speed to generate suction at the blower fan, the suction at the blower fan conducted to the filter cartridge within the sequestration channel via the conduit;
  draw the WAGs through the filter cartridge using the suction from the blower fan; and
  return the blower fan to a nominal operating speed responsive to no longer identifying the emission of WAGs external to the anesthetic vaporizer.

12. They system of claim 9, wherein the suction source includes an active scavenging system of an anesthesia machine mated with the anesthetic vaporizer, the active scavenging system including an adsorbent filter, and the instructions that cause the controller to perform at least one of outputting the alert and scavenging the WAGs by applying suction from the suction source to the sequestration channel via the conduit include further instructions stored in non-transitory memory that, when executed, cause the controller to:
  conduct the suction from the active scavenging system to the sequestration channel by opening one or more valves disposed in the conduit;
  draw the WAGs through the sequestration channel and to the adsorbent filter using the suction from the active scavenging system; and
  close the one or more valves responsive to no longer identifying the emission of WAGs external to the anesthetic vaporizer.

13. A non-transitory computer-readable medium comprising instructions that, when executed, cause a processor to:
  detect an emission of waste anesthetic gases (WAGs) by an anesthetic vaporizer based on output received from one or more sensors; and
  responsive to detecting the emission of WAGs, perform at least one of scavenging the WAGs and outputting an alert,
  wherein the one or more sensors include an external sensor located on an exterior of the anesthetic vaporizer, and to perform at least one of scavenging the WAGs and outputting the alert, the instructions, when executed, cause the processor to:
    apply suction to a sequestration channel included in a filler apparatus of the anesthetic vaporizer from a suction source fluidically coupled to the sequestration channel via a conduit responsive to the external sensor indicating the emission of WAGs from the anesthetic vaporizer; and
    draw the WAGs through an adsorbent filter fluidically coupled to the sequestration channel using the suction.

14. The computer-readable medium of claim 13, wherein the suction source includes a suctioner positioned within the anesthetic vaporizer, and to apply the suction to the sequestration channel, the instructions, when executed, cause the processor to increase an operating speed of the suctioner to increase the suction applied to the sequestration channel.

15. The computer-readable medium of claim 13, wherein the suction source includes a scavenging system located external to the anesthetic vaporizer, and to apply the suction to the sequestration channel, the instructions, when executed, cause the processor to open one or more valves positioned in the conduit coupling the sequestration channel to the suction source.

16. The computer-readable medium of claim 13, wherein the one or more sensors include a volatile organic compound (VOC) sensor located internally within the anesthetic vaporizer, and to perform at least one of scavenging the WAGs and outputting the alert, the instructions, when executed, cause the processor to output the alert responsive to a level of WAGs measured by the VOC sensor increasing above a threshold.

* * * * *